(12) United States Patent
Korfhage et al.

(10) Patent No.: US 9,005,933 B2
(45) Date of Patent: Apr. 14, 2015

(54) HELICASE DEPENDENT ISOTHERMAL AMPLIFICATION USING NICKING ENZYMES

(75) Inventors: Christian Korfhage, Langenfeld (DE); Gerd Grosshauser, Pulheim (DE); Thomas Rothmann, Langenfeld (DE); Ralf Himmelreich, Langenfeld (DE)

(73) Assignee: Qiagen GmbH, Hilden (DE)

( * ) Notice: Subject to any disclaimer, the term of this patent is extended or adjusted under 35 U.S.C. 154(b) by 124 days.

(21) Appl. No.: 13/817,174

(22) PCT Filed: Aug. 16, 2011

(86) PCT No.: PCT/EP2011/064114
§ 371 (c)(1),
(2), (4) Date: Apr. 11, 2013

(87) PCT Pub. No.: WO2012/022755
PCT Pub. Date: Feb. 23, 2012

(65) Prior Publication Data
US 2013/0210019 A1    Aug. 15, 2013

Related U.S. Application Data

(60) Provisional application No. 61/374,506, filed on Aug. 17, 2010.

(30) Foreign Application Priority Data

Aug. 17, 2010   (EP) ..................................... 10173094

(51) Int. Cl.
   *C12P 19/34*   (2006.01)
   *C12Q 1/68*    (2006.01)

(52) U.S. Cl.
   CPC ................................... *C12Q 1/6844* (2013.01)

(58) Field of Classification Search
   CPC ........... C12Q 1/6844; C12Q 2521/301; C12Q 2521/513
   USPC ................................................. 435/91.2, 6.1
   See application file for complete search history.

(56) References Cited

U.S. PATENT DOCUMENTS

| | | | |
|---|---|---|---|
| 5,455,166 A | 10/1995 | Walker | |
| 5,716,819 A | 2/1998 | Chatterjee | |
| 6,214,587 B1 | 4/2001 | Dattagupta et al. | |
| 6,555,349 B1 | 4/2003 | O'Donnell | |
| 7,282,328 B2 * | 10/2007 | Kong et al. | .................. 435/6.12 |
| 2003/0082590 A1 | 5/2003 | Van Ness et al. | |
| 2009/0017453 A1 | 1/2009 | Maples et al. | |

FOREIGN PATENT DOCUMENTS

| | | |
|---|---|---|
| EP | 1539979 | 11/2008 |
| WO | WO2004022701 | 3/2004 |
| WO | WO2004027025 A2 | 4/2004 |
| WO | WO2004067726 | 8/2004 |
| WO | WO2006074334 | 7/2006 |
| WO | WO2009012246 | 1/2009 |
| WO | WO2010091111 A1 | 8/2010 |
| WO | WO 2011/085160 | 7/2011 |

OTHER PUBLICATIONS

Vincent, et al., EMBO; vol. 5, No. 8, 2004, pp. 795-800.
Jeong, el al., Cell. Mol. Life Sci., vol. 66, 2009, pp. 3325-3336.
Van Ness, et al., Proc. Natl. Acad. Sci., vol. 100, No. 8, 2003, pp. 4504-4509.
Harmon, et al., J. Biol. Chem., vol. 276, 2001, pp. 323-343.
Collins, et al., Extremophiles, vol. 7, 2003, pp. 35-41.
Kaplan, et al., J. Biol. Chem., vol. 274, 1999, pp. 6889-6897.
Grainge, et al., Nucleic Acids Research, vol. 31, 2003, pp. 4888-4896.
Keohavong, et al., Proc. Natl. Acad. Sci., vol. 86, 1989, pp. 9253-9257.
Kampke, et al., Bioinformatics, vol. 17, 2003, pp. 214-225.
Lee, et al., J. Mol. Biol., vol. 316, 2002, pp. 19-34.
Jessing, et al., J. Clin. Micbrobiol., vol. 41, 2003, pp. 4095-4100.

* cited by examiner

*Primary Examiner* — Cynthia B Wilder
(74) *Attorney, Agent, or Firm* — Fanelli Haag & Kilger PLLC

(57) ABSTRACT

The present invention relates to a method for amplifying a template nucleic acid, wherein the method comprises amplifying said template nucleic acid using the helicase dependent amplification (HDA) reaction in the presence of a nicking endonuclease, and wherein said template nucleic acid comprises a sequence recognized by said nicking endonuclease or a sequence recognized by said nicking endonuclease is introduced into the template nucleic acid during the HDA reaction. The invention further pertains to a kit for amplifying a nucleic acid, comprising a nicking endonuclease, a helicase and a DNA polymerase.

19 Claims, 14 Drawing Sheets

322-atttgatgctgtcccggacgatattgaacaatgttcactgaagaccccaggtccccagaatg-395 SEQ ID No.6
5'-atttgatgctgtcccggacgatatt-3' SEQ ID No.7          3'-gtccaggtctacttcgagggtcttac-5' SEQ ID No.8
Primer HDA-TP53 for                                    Primer HDA-TP53 rev 3'-gtccaggtctact[ct]gagggtcttac-5'  SEQ ID No.9
                        Primer HDA-TP53 rev7

☐ Nt.BstNBI recognition site
▼ Nt.BstNBI hydrolysis site

SEQUENCE LISTING

<160> NUMBER OF SEQ ID NOS: 10

<210> SEQ ID NO 1
<211> LENGTH: 82

```
<212> TYPE: DNA
<213> ORGANISM: Neisseria gonorrhoeae

<400> SEQUENCE: 1
atttgttccg agtcaaaaca gcaagtccgc ctatacgcct gctactttca cgctggaaag      60
taatcagatg aaaccagttc cg                                               82

<210> SEQ ID NO 2
<211> LENGTH: 27
<212> TYPE: DNA
<213> ORGANISM: Artificial Sequence
<220> FEATURE:
<223> OTHER INFORMATION: Description of Artificial Sequence: Synthetic
      primer/probe

<400> SEQUENCE: 2
atttgttccg agtcaaaaca gcaagtc                                          27

<210> SEQ ID NO 3
<211> LENGTH: 27
<212> TYPE: DNA
<213> ORGANISM: Artificial Sequence
<220> FEATURE:
<223> OTHER INFORMATION: Description of Artificial Sequence: Synthetic
      primer/probe

<400> SEQUENCE: 3
cggaactggt ttcatctgat tactttc                                          27

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: Synthetic
      primer/probe

<400> SEQUENCE: 4
cgcctatacg cctgctactt tcacg                                            25

<210> SEQ ID NO 5
<211> LENGTH: 50
<212> TYPE: DNA
<213> ORGANISM: Artificial Sequence
<220> FEATURE:
<223> OTHER INFORMATION: Description of Artificial Sequence: Synthetic
      primer/probe

<400> SEQUENCE: 5
cggggcgtct ggaaggcgca ttccggaact ggtttcatct gattactttc                 50

<210> SEQ ID NO 6
<211> LENGTH: 74
<212> TYPE: DNA
<213> ORGANISM: Homo sapiens

<400> SEQUENCE: 6
atttgatgct gtccccggac gatattgaac aatggttcac tgaagaccca ggtccagatg      60
aagctcccag aatg                                                        74

<210> SEQ ID NO 7
<211> LENGTH: 26
<212> TYPE: DNA
<213> ORGANISM: Artificial Sequence
<220> FEATURE:
```

```
<223> OTHER INFORMATION: Description of Artificial Sequence: Synthetic
      primer/probe

<400> SEQUENCE: 7
atttgatgct gtccccggac gatatt                                            26

<210> SEQ ID NO 8
<211> LENGTH: 26
<212> TYPE: DNA
<213> ORGANISM: Artificial Sequence
<220> FEATURE:
<223> OTHER INFORMATION: Description of Artificial Sequence: Synthetic
      primer/probe

<400> SEQUENCE: 8
cattctggga gcttcatctg gacctg                                            26

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Synthetic
      primer/probe

<400> SEQUENCE: 9
cattctggga gtctcatctg gacctg                                            26

<210> SEQ ID NO 10
<211> LENGTH: 105
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 10
atttgttccg agtcaaaaca gcaagtccgc ctatacgcct gctactttca cgctggaaag       60
taatcagatg aaaccagttc cggaatgcgc cttccagacg ccccg                       105
```

HELICASE DEPENDENT ISOTHERMAL AMPLIFICATION USING NICKING ENZYMES

This application is a National Stage of PCT/EP2011/064114, filed Aug. 16, 2011 which claims priority to U.S. Provisional Application No. 61/374,506, filed Aug. 17, 2010 and European Application No. 10173094.3, filed Aug. 17, 2010, the disclosures of which are incorporated herein by reference in their entirety.

FIELD OF THE INVENTION

The present invention is in the field of biology and chemistry, particularly in the field of molecular biology. More in particular, the invention relates to a method and a kit for the amplification of nucleic acids.

The instant application contains a Sequence Listing which has been submitted in ASCII format via EFS-Web and is hereby incorporated by reference in its entirety. Said ASCII copy, created on Feb. 11, 2013, is named 0051_0078_US1_Sequence_Listing.txt and is 1999 bytes in size.

The instant application contains a Sequence Listing which has been submitted in ASCII format via EFS-Web and is hereby incorporated by reference in its entirety. Said ASCII copy, created on Nov. 12, 2014, is named 00510078US1 SL.txt and is 2,831 bytes in size.

BACKGROUND OF THE INVENTION

Amplification of nucleic acids is widely used in research, diagnostics, forensics, medicine, food science and agriculture. "Point of Care Testing" (POCT) relates to diagnostic testing at or near the site of patient care, i.e. de-centralized examinations that may e.g. be performed in private medical practices, small hospitals, pharmacies, or even in the field or at the site of an accident or other medical emergency or within an ambulance. Point-of-care diagnostics requires rapid and easy testing. Hence, in the case of nucleic-acid based detection methods, fast isothermal amplification technologies have recently become more and more important as compared to the established but slower PCR-based methods. PCR requires thermo-cycling in order to separate the two strands of double-stranded nucleic acids such as DNA. In contrast, isothermal amplification methods for example do not require a thermocycler.

One of the most prominent isothermal amplification methods is the so-called Helicase Dependent Amplification (HDA) (described e.g. in Vincent et al. (2004), EMBO reports 5(8): 795-800; Jeong et al. (2009), Cell. Mol. Life. Sci 66:3325-3336; WO-A2 2004/027025; WO-A2 2006/074334; all incorporated by reference herein). HDA is based on the ability of helicases to unwind double-stranded nucleic acids, particularly DNA, without the need for heating or even thermocycling. In HDA, the separated DNA strands are replicated using DNA polymerases and suitable oligonucleotide primers. Hence, HDA mimics the natural replication fork mechanism. HDA requires the presence of ATP, divalent magnesium ions and dNTPs. Some HDA-based methods additionally employ single-stranded binding proteins (SSBs) for the coating of displaced DNA strands. In principal HDA methods can be performed in thermolabile or thermostable reactions depending on the enzymes used. Thermolabile HDA reactions are typically performed at temperatures between 25 and 50° C., preferably between 37 and 42° C. In contrast the thermostable HDA or thermophilic HDA (tHDA) reactions are performed at temperatures above 50° C., typically between 60 and 70° C.

The HDA reaction selectively amplifies a target sequence defined by two primers. HDA uses a helicase enzyme to separate the two strands of double-stranded nucleic acid rather than heat as in PCR. Therefore, HDA can be performed at a single temperature without the need of thermocycling. The steps of a conventional standard HDA reaction are shown in FIG. 1: In the first step a double-stranded nucleic acid is unwound by a helicase resulting in (partially) single-stranded sequences. This is followed by binding of primers to the single-stranded regions. In step 2 a polymerase synthesizes complementary strands. Ultimately, the helicase and the polymerase act together to result in amplification of the template (step 3).

Other isothermal amplification include Strand Displacement Amplification (SDA) which is based on nicking an unmodified strand of DNA using restriction enzymes and extending the 3' end at the nick through the action of an exonuclease deficient DNA polymerase to displace the downstream DNA strand.

Yet another isothermal amplification is the Rolling Circle Amplification (RCA) in which a linear ssDNA is annealed to a circular ssDNA template which has been generated by joining two ends of the template DNA using a DNA ligase. Subsequently, the annealed primer is extended using a DNA polymerase and tandemly linked copies of the complementary template sequence are generated. RCA and SDA both require an initial heat denaturation step.

Other isothermal amplification include for example the Nicking Enzyme Amplification Reaction (NEAR) and the related Exponential Amplification Reaction (EXPAR) which both employ nicking enzymes and polymerases for the amplification of short double-stranded template sequences (described e.g. in van Ness et al. (2003), Proc. Natl. Acad. Sci. 100(8):4504-4509; US-A1 2003/0082590; WO-A2 2004/022701; WO-A2 2009/012246; WO-A2 2004/067726; all incorporated by reference herein).

However, all of the above-described isothermal amplification methods require complicated reaction protocols, are relatively slow and/or are limited to relatively short template sequences.

SUMMARY OF THE INVENTION

The present invention provides for an improved method for amplification of nucleic acids, preferably double-stranded nucleic acids, that overcomes these limitations of the prior art. The inventive method is based on a modified HDA method. The provided method is faster than conventional tHDA and has at the same time a reliable specificity. Compared to methods like NEAR and EXPAR, the method of the present invention can amplify longer template nucleic acids.

The present invention relates to a HDA amplification method that is performed in the presence of a nicking endonuclease. Hence, in the context of the present invention template nucleic acids are amplified in the presence of a helicase, a suitable polymerase, and a nicking endonuclease.

In particular, the present invention relates to a method for amplifying a template nucleic acid, particularly DNA,
wherein the method comprises amplifying said template nucleic acid using the helicase dependent amplification (HDA) reaction, particularly a thermophilic HDA (tHDA), in the presence of a nicking endonuclease, and
wherein said template nucleic acid comprises a sequence recognized by said nicking endonuclease or a sequence recognized by said nicking endonuclease is introduced into the template nucleic acid during the HDA reaction.

The sequence recognized by a nicking endonuclease can be introduced into the template nucleic acid using an oligonucleotide primer comprising the sequence recognized by a nicking endonuclease. Such a primer may comprise a 5' tag sequence that does not hybridize to the template nucleic acid but comprises the sequence recognized by a nicking endonuclease or a part thereof.

The invention further pertains to a kit for amplifying a nucleic acid, comprising
  a nicking endonuclease,
  a helicase, and
  a DNA polymerase.

The method and kit of the present invention may be used in the amplification of nucleic acids but also for the detection and/or quantification of nucleic acids.

DETAILED DESCRIPTION OF THE INVENTION

Figure 1:
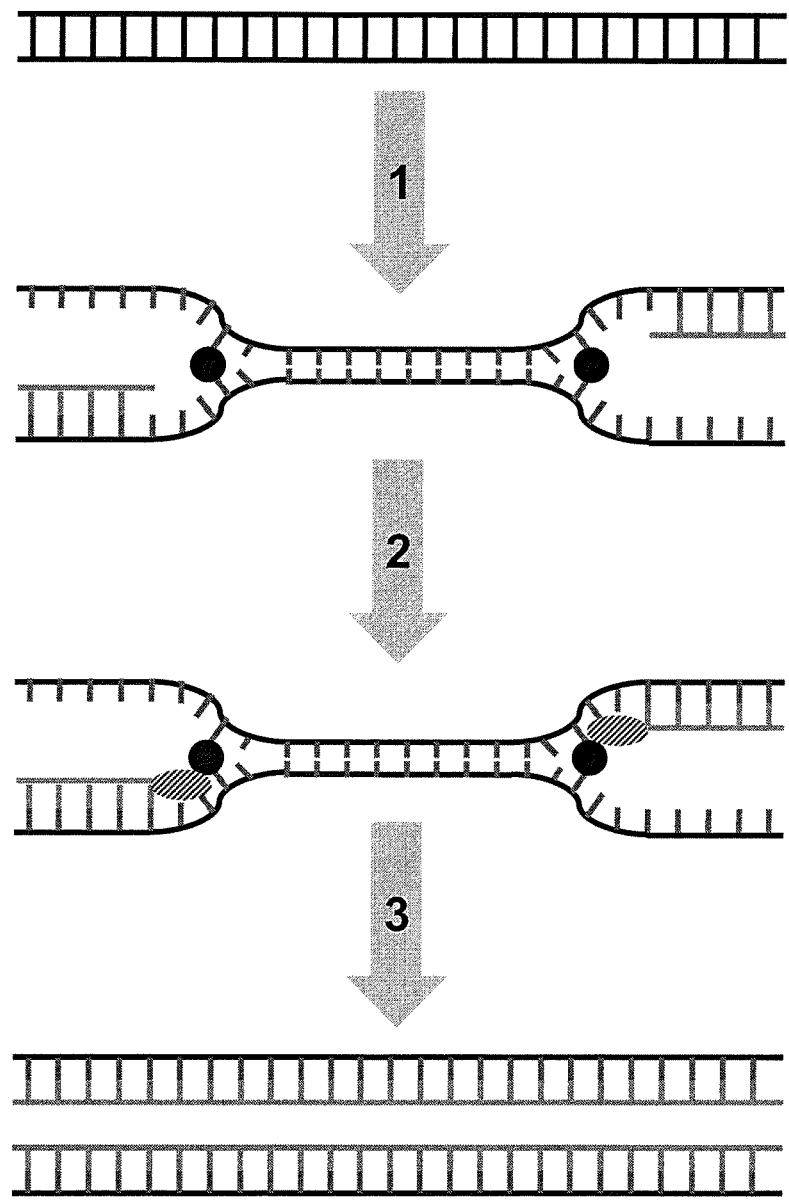
FIG. 1 shows a scheme of the standard tHDA reaction according to the prior art and as commercially available e.g. from biohelix/New England Biolabs, i.e. in the absence of a nicking endonuclease.

The present invention provides a method and a kit for the amplification and optionally detection of nucleic acid, particularly DNA. The method of the invention is based on the helicase-dependent amplification (HDA) reaction. However, unlike in the HDA reactions of the prior art, in the amplification reaction according to the present invention a nicking endonuclease is present. Hence, the kits of the present invention also comprise a nicking endonuclease. The method of the present invention may herein be referred to as "nicking HDA".

The method and kits according to the present invention are particularly useful for the amplification and detection of short DNA sequences, preferably sequences of less than 400 bp, more preferably less than 200 bp, even more preferably 150 bp or less, most preferably between 70 and 120 bp. Typically, with the methods and kits of the present invention double-stranded nucleic acids are amplified or detected. However, also single-stranded nucleic acids can be amplified and detected as long as they are transcribed into a nucleic acid duplex, i.e. a double-stranded template, by means of a polymerase before the actual HDA-based amplification begins.

In particular the present invention pertains to a method for amplifying a template nucleic acid,
  wherein the method comprises amplifying said template nucleic acid using the helicase dependent amplification (HDA) reaction in the presence of a nicking endonuclease, and
  wherein said template nucleic acid comprises a sequence recognized by said nicking endonuclease or a sequence recognized by said nicking endonuclease is introduced into the template nucleic acid during the HDA reaction.

The method and kits can be used with a variety of template nucleic acids, preferably with double-stranded nucleic acids. Typically, DNA will be amplified and or detected with the kits and methods of the present invention. Hence, in the context of the present invention the template nucleic acid is preferably a double-stranded nucleic acid and more preferably a DNA.

The sequences to be amplified or detected may for example be in a linear or circular DNA. The DNA may for instance be selected from genomic DNA, e.g. microbial genomic DNA, viral DNA, plasmid DNA and cDNA. The template may be reverse transcribed from a RNA, particularly mRNA.

In the context of the present invention, 'dsDNA' and 'DNA' duplex relate to double-stranded DNA, 'ssDNA' relates to single-stranded DNA, 'dsRNA' relates to double-stranded RNA and 'ssRNA' relates to single-stranded RNA.

Other nucleic acids such as dsRNA or DNA/RNA hybrids may also be amplified with the kits and methods of the invention. Other enzymatic steps such as reverse transcription or in vitro-transcription may be performed prior to HDA to form addressable nucleic acids.

The present invention requires the presence of a sequence that is recognized by a nicking endonuclease in the template nucleic acid that is to be amplified. Since not every target sequence to be amplified comprises such a nicking endonuclease recognition sequence, such sequences can be introduced by suitable primers.

Hence, in preferred embodiments of the method of the invention, the sequence recognized by a nicking endonuclease is introduced into the template nucleic acid using an oligonucleotide primer comprising the sequence recognized by a nicking endonuclease.

Figure 2:
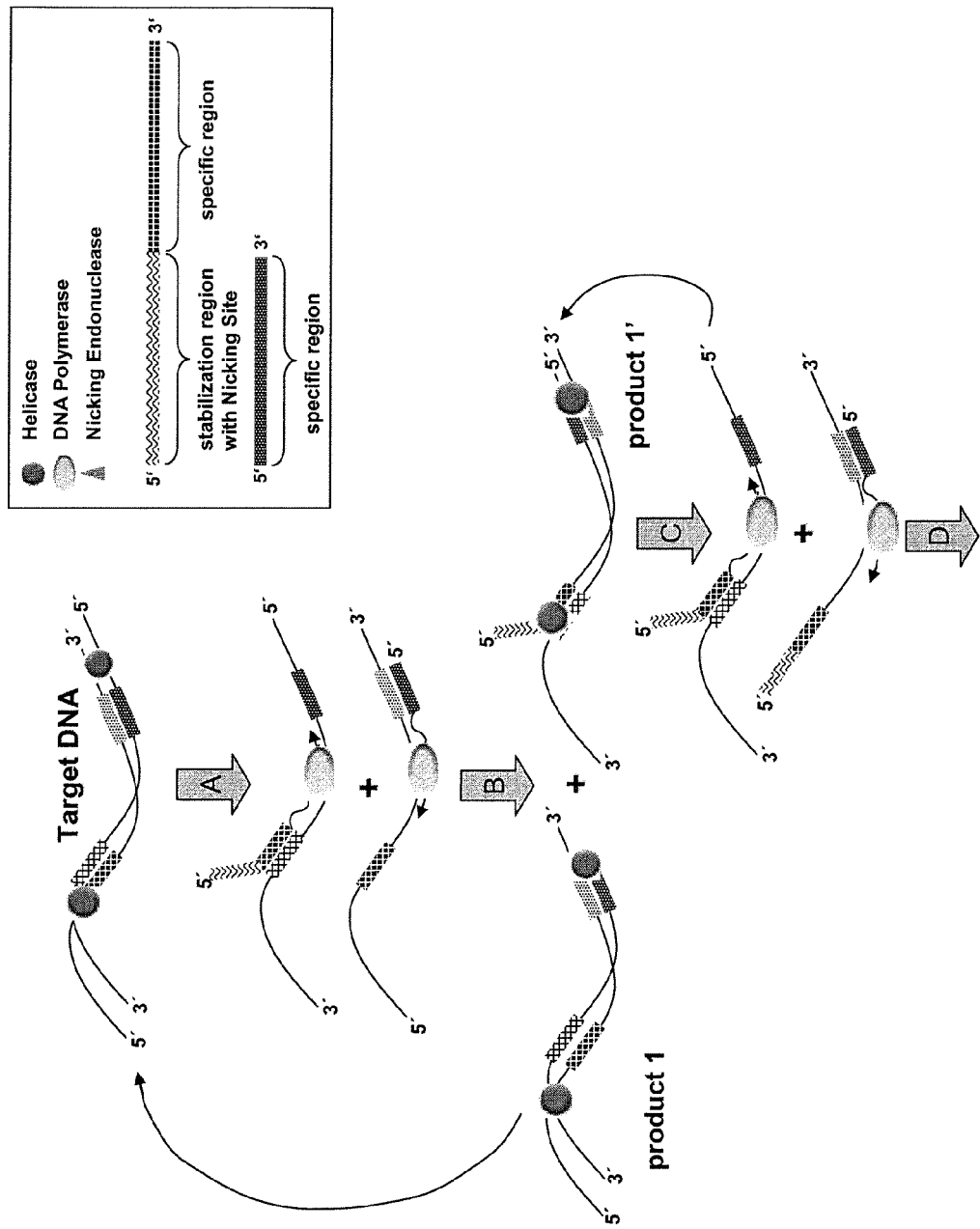
FIG. 2 illustrates the reaction scheme according to a particular embodiment of the nicking tHDA of the invention using a tagged primer.
Figure 2:
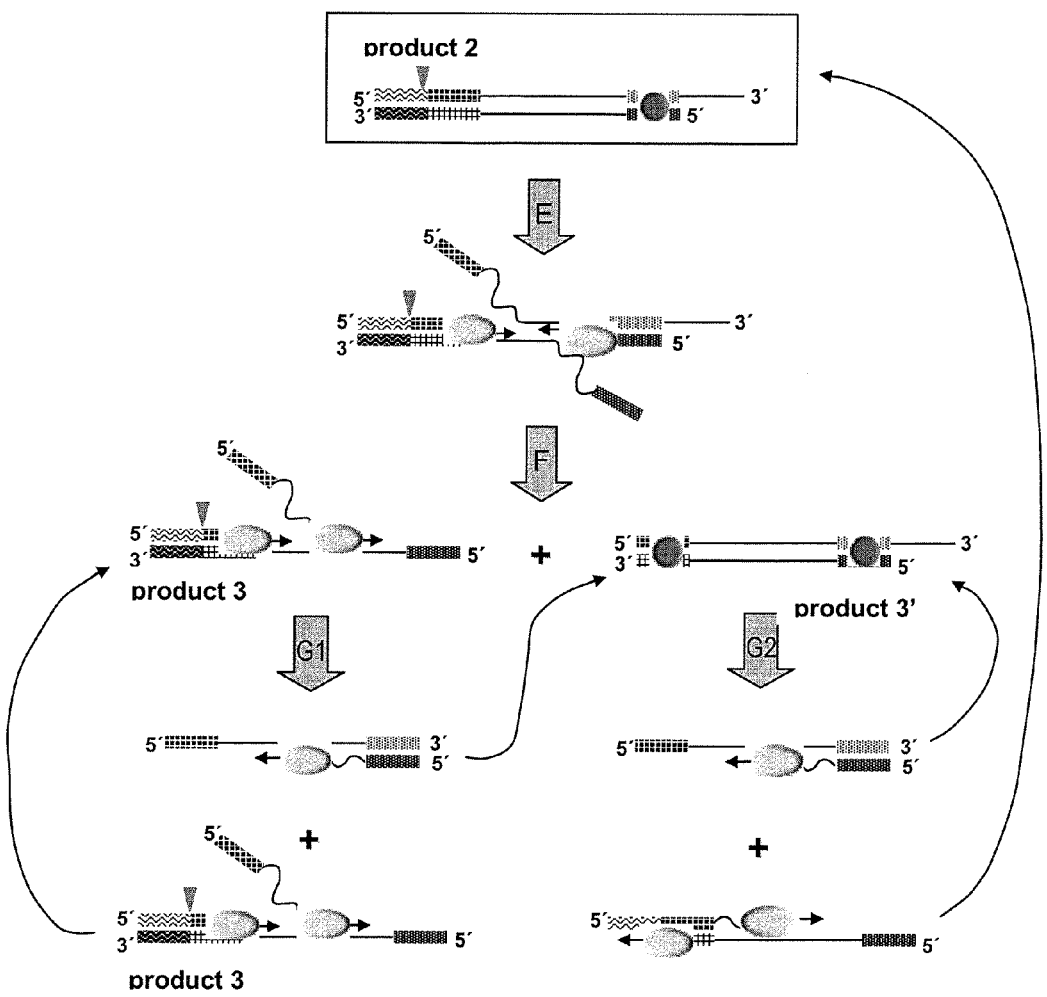

In a certain embodiment the primer comprising the sequence recognized by a nicking endonuclease comprises a 5' tag sequence that does not hybridize to the template nucleic acid and the sequence recognized by a nicking endonuclease is in said tag sequence. Such primers are herein designated "tagged primers" and a corresponding embodiment is schematically illustrated in FIG. 2.

Also mutagenic primers may be employed, i.e. primers that are not 100% complementary to the original template sequence thereby introducing a suitable recognition sequence of a nicking endonuclease.

The HDA reaction of the invention is preferably a thermophilic HDA (tHDA), i.e. the enzymes used are thermostable at the temperatures of the method. Thermostable enzymes to typically are enzymes originating from thermostable organisms. Hence, the method of the present invention is preferably performed at a temperature above 60° C., more preferably between 60 and 70° C., even more preferably between 60 and 65° C. and most preferably at around 64 to 65° C. The temperature may be maintained for example using a water bath, a heating block, an incubator or a thermocycler.

The method of the invention is generally an isothermal method, meaning that the method is performed at a single temperature without the need of temperature cycling as for example in PCR. However, in certain embodiments of the invention, a heat denaturation step at high temperatures, typically above 90° C., preferably at around 95° C., may be included before the reaction is performed at the constant actual reaction temperature. This is then referred to as a 'two-step' reaction in contrast to the 'one-step' protocol which is performed at a single temperature. Under certain circumstances the two-step protocol may result in higher sensitivities. Therefore a two-step protocol is preferred in the context of the present invention.

In principal, in the nicking HDA method according to the invention, a template nucleic acid is incubated in the presence of a helicase, a polymerase, a nicking enzyme and suitable forward and reverse oligonucleotide primers. Additionally further reagents such as dNTPs, ATP or dATP and magnesium ions need to be present for the amplification reaction. The reaction mix preferably also comprises a buffering agent and salts such as NaCl and/or KCl.

The individual enzymes and reagents may be added together before the start of the amplification or the may be added sequentially. In some particular embodiments, the nicking endonuclease is added after the other components. In preferred embodiments of the two-step protocol, the enzymes are added after the initial heat denaturation step.

The term "primer" refers to a single stranded nucleic acid capable of binding to a single stranded region on a target nucleic acid to facilitate polymerase dependent replication of the target nucleic acid. In the context of the present invention, one or more primers are added to the template nucleic acid. The use of one primer leads to linear amplification, while the use of two or even more primers results in exponential amplification.

The term "helicase" refers here to any enzyme capable of unwinding a double stranded nucleic acid enzymatically. For example, helicases are enzymes that are found in all organisms and in all processes that involve nucleic acid such as replication, recombination, repair, transcription, translation and RNA splicing. (Kornberg and Baker, DNA Replication, W.H. Freeman and Company (2nd ed. (1992)), especially chapter 11). Any helicase that translocates along DNA or RNA in a 5' to 3' direction or in the opposite 3' to 5' direction may be used in present embodiments of the invention. This includes helicases obtained from prokaryotes, viruses, archaea, and eukaryotes or recombinant forms of naturally occurring enzymes as well as analogues or derivatives having the specified activity. Examples of naturally occurring DNA helicases, described by Kornberg and Baker in chapter 11 of their book, DNA Replication, W.H. Freeman and Company (2nd ed. (1992)), include *E. coli* helicase I, II, III, & IV, Rep, DnaB, PriA, PcrA, T4 Gp41 helicase, T4 Dda helicase, T7 Gp4 helicases, SV40 Large T antigen, yeast RAD. Additional helicases that may be useful in HDA include RecQ helicase (Harmon and Kowalczykowski, J. Biol, Chem. 276: 232-243 (2001)), thermostable UvrD helicases from *T. tengcongensis* and *T. thermophilus* (Collins and McCarthy, Extremophiles. 7: 35-41. (2003)), thermostable DnaB helicase from *T. aquaticus* (Kaplan and Steitz, J. Biol. Chem. 274: 6889-6897 (1999)), and MCM helicase from archaeal and eukaryotic organisms (Grainge et al., Nucleic Acids Res. 31: 4888-4898 (2003)).

Examples of helicases that generally replicate in a 5' to 3' direction are T7 Gp4 helicase, DnaB helicase and Rho helicase, while examples of helicases that replicate in the 3'-5' direction include UvrD helicase, PcrA, Rep, NS3 RNA helicase of HCV.

Helicases may require cofactors, i.e. small-molecule agents that are required for the helicase unwinding activity. Helicase cofactors include nucleoside triphosphate (NTP) and deoxynucleoside triphosphate (dNTP) and magnesium (or other divalent cations). For example, ATP (adenosine triphosphate) may be used as a cofactor for UvrD helicase at a concentration in the range of 0.1-100 mM and preferably in the range of 1 to 10 mM (for example 3 mM). Similarly, dTTP (deoxythymidine triphosphate) may be used as a cofactor for T7 Gp4B helicase in the range of 1-10 mM (for example 3 mM).

In some embodiments of the invention, particularly for non-thermophile HDA, additional proteins such as a topoisomerase or accessory proteins such as single-strand DNA binding proteins (SSBs) may be present in the reaction in order to facilitate helicase activity. Helicases show improved activity in the presence of single-strand binding proteins (SSB). In these circumstances, the choice of SSB is generally not limited to a specific protein. Examples of single strand binding proteins are T4 gene 32 protein, *E. coli* SSB, T7 gp2.5 SSB, phage phi29 SSB (Kornberg and Baker, supra (1992)) and truncated forms of the aforementioned. Where a thermostable helicase is used, the presence of one or more SSBs or other accessory proteins is optional.

Helicases and preparations comprising helicases for use in HDA and tHDA are described in more detail in EP-B1 1 539 979, particularly in sections [0039] to [0066].

The nicking HDA amplification reaction according to the present is preferably performed at a temperature above 50° C., preferably between 50 and 70° C., more preferably between 60 and 65° C.

In the context of the present invention, the helicase can be from different families of helicases. The helicase is preferably selected from the group consisting of superfamily I helicases, superfamily II helicases, superfamily III helicases, helicases from dnaB-like superfamily or helicases form rho-like superfamily. The helicases may be derived from mesophilic or heat tolerant organisms. The helicases may be genetically or chemically modified. Superfamily I helicases e.g. include dda, perA, F-plasmid traI protein helicase and UvrD. Superfamily II helicases e.g. include recQ and NS3-helicase. Superfamily III helicases e.g. include AAV rep helicase. Helicases from dnaB-like superfamily e.g. include T7 phage helicase. It is preferred in the context of the methods and kits of the present invention that the helicase is a thermostable helicase. The thermostable Tte-UvrD helicase is preferred.

Topoisomerase can be used in long HDA reactions to increase the ability of HDA to amplify long target amplicons. When a very long linear DNA duplex is separated by a helicase, the swivel (relaxing) function of a topoisomerase removes the twist and prevents over-winding (Kornberg and Baker, supra (1992)). For example, $E.$ $coli$ topoisomerase I (Fermentas, Vilnius, Lithuania) can be used to relax negatively supercoiled DNA by introducing a nick into one DNA strand. In contrast, $E.$ $coli$ DNA gyrase (topoisomerase II) introduces a transient double-stranded break into DNA allowing DNA strands to pass through one another (Kornberg and Baker, supra (1992)).

In principal all polymerases may be selected that are active at the desired reaction temperature, i.e. that are able to elongate free 3'-OH ends. Also polymerases that have additional functionalities such as proof-reading function, endonuclease activity, strand displacement activity and/or reverse transcriptase activity can be used in the context of the present invention. Polymerases are selected for HDA on the basis of processivity and strand displacement activity. Subsequent to melting and hybridization with a primer, the nucleic acid is subjected to a polymerization step. A DNA polymerase is selected if the nucleic acid to be amplified is DNA. When the initial target is RNA, a reverse transcriptase is used first to copy the RNA target into a cDNA molecule and the cDNA is then further amplified in HDA by a selected DNA polymerase. The DNA polymerase acts on the target nucleic acid to extend the primers hybridized to the nucleic acid templates in the presence of four dNTPs to form primer extension products complementary to the nucleotide sequence on the nucleic acid template.

The DNA polymerase is selected from a group of polymerases lacking 5' to 3' exonuclease activity and which additionally may optionally lack 3'-5' exonuclease activity.

Examples of suitable DNA polymerases include an exonuclease-deficient Klenow fragment of $E.$ $coli$ DNA polymerase I (New England Biolabs, Inc. (Beverly, Mass.)), an exonuclease deficient T7 DNA polymerase (Sequenase; USB, (Cleveland, Ohio)), Klenow fragment of $E.$ $coli$ DNA polymerase I (New England Biolabs, Inc. (Beverly, Mass.)), Large fragment of Bst DNA polymerase (New England Biolabs, Inc. (Beverly, Mass.)), KlenTaq DNA polymerase (AB Peptides, (St Louis, Mo.)), T5 DNA polymerase (U.S. Pat. No. 5,716,819), and Pol III DNA polymerase (U.S. Pat. No. 6,555,349). DNA polymerases possessing strand-displacement activity, such as the exonuclease-deficient Klenow fragment of $E.$ $coli$ DNA polymerase I, Bst DNA polymerase Large fragment, and Sequenase, are preferred in the context of the present invention. T7 polymerase is a high fidelity polymerase having an error rate of $3.5 \times 10^5$ which is significantly less than Taq polymerase (Keohavong and Thilly, Proc. Natl. Acad. Sci. USA 86, 9253-9257 (1989)). T7 polymerase is not thermostable however and therefore is not optimal for use in amplification systems that require thermocycling. In HDA, which can be conducted isothermally, T7 Sequenase is a one of the preferred polymerases for amplification of DNA.

In the context of the methods and kits of the invention the polymerase is preferably a thermostable polymerase. Preferably the polymerase is selected from the group consisting of Bst DNA polymerase, PyroPhage polymerase, DisplaceAce polymerase and Vent (exo-) Polymerase Polymerases that have no considerable exonuclease activity are preferred.

Generally, primers suitable for use in HDA and nicking HDA are short synthetic oligonucleotides, for example, having a length of more than 10 nucleotides and less than 50 nucleotides. Oligonucleotide primer design involves various parameters such as string-based alignment scores, melting temperature, primer length and GC content (Kampke et al., Bioinformatics 17: 214-225 (2003)). When designing a primer, one of the important factors is to choose a sequence within the target fragment which is specific to the nucleic acid molecule to be amplified. The other important factor is to decide the melting temperature of a primer for HDA reaction. The melting temperature of a primer is determined by the length and GC content of that oligonucleotide. Preferably the melting temperature of a primer is in the range of the temperature at which the hybridization and amplification will take place. For example, if the temperature of the hybridization and amplification is set at 37° C. when using the $E.$ $coli$ UvrD helicase preparation, the melting temperature of a pair of primers designed for this reaction should be in a range between about 30° C. to 50° C. If the temperature of the hybridization and amplification is 60° C., the melting temperature of a pair of primers designed for that reaction should be in a range between 55° C. and 70° C., preferably between 55° C. and 65° C. Primers with melting temperatures considerably higher than the reaction temperature may result in unspecific side reactions and are therefore less preferred. To choose the best primer for a HDA reaction, a set of primers with various melting temperatures can be tested in a parallel assay. More information regarding primer design is described by Kampke et al., Bioinformatics 17:214-225 (2003). Each primer hybridizes to each end of the target nucleic acid and may be extended in a 3' to 5' direction by a polymerase using the target nucleotide sequence as a template. Conditions of hybridization are standard as described in "Molecular Cloning and Laboratory Manual" 2nd ed. Sambrook, Rich and Maniatis, pub. Cold Spring Harbor (2003). To achieve specific amplification, a homologous or perfect match primer is preferred. However, primers may include sequences at the 5' end which are non complementary to the target nucleotide sequence(s). Alternatively, primers may contain nucleotides or sequences throughout that are not exactly complementary to the target nucleic acid. Primers may represent analogous primers or may be non-specific or universal primers for use in HDA as long as specific hybridization can be achieved by the primer-template binding at a predetermined temperature.

The primers may include any of the deoxyribonucleotide bases A, T, G or C and/or one or more ribonucleotide bases, A, C, U, G and/or one or more modified nucleotide (deoxyribonucleotide or ribonucleotide) wherein the modification does not prevent hybridization of the primer to the nucleic acid or elongation of the primer or denaturation of double-stranded molecules. Primers may be modified with chemical groups such as phosphorothioates or methylphosphonates or with non nucleotide linkers to enhance their performance or to facilitate the characterization of amplification products.

To detect amplified products, the primers may be subject to modification, such as fluorescent or chemiluminescent-labeling, and biotinylation. Other labeling methods include radio-active isotopes, chromophores and ligands such as biotin or haptens which while not directly detectable can be readily detected by reaction with labeled forms of their specific binding partners e.g. avidin and antibodies respectively. Primers as described herein can be prepared by methods known in the art. (see, for example U.S. Pat. No. 6,214,587). In some embodiments, a pair of two sequence-specific primers, one hybridizing to the 5'-border of the target sequence and the other hybridizing to the 3'-border of the target are used in the method of the invention to achieve exponential amplification of a target sequence. This approach can be readily distinguished from Lee et al. (J. Mol. Biol. 316: 19-34 (2002)). Multiple pairs of primers can be utilized in a single HDA reaction for amplifying multiple targets simultaneously using different detection tags in a multiplex reaction. Multiplexing is commonly used in SNP analysis and in detecting pathogens (Jessing et al., J. Clin. Microbiol. 41:4095-4100 (2003)).

tHDA primers can for example be designed using the PrimerQuest program or the Primer3 program.

As used herein, "nicking" refers to the cleavage of only one strand of a fully double-stranded nucleic acid molecule or a double-stranded portion of a partially double-stranded nucleic acid molecule at a specific position relative to a nucleotide sequence that is recognized by the enzyme that performs the nicking. The specific position where the nucleic acid is nicked is referred to as the "nicking site".

A "nicking endonuclease" is an enzyme that recognizes a particular nucleotide sequence of a completely or partially double-stranded nucleic acid molecule and cleaves only one strand of the nucleic acid molecule at a specific position relative to the recognition sequence. A "nicking endonuclease", as used herein, refers to an endonuclease that recognizes a nucleotide sequence of a completely or partially double-stranded nucleic acid molecule and cleaves only one strand of the nucleic acid molecule at a specific location relative to the recognition sequence. A restriction endonuclease typically recognizes a nucleotide sequence composed of only native nucleotides and cleaves only one strand of a fully or partially double-stranded nucleic acid molecule that contains the nucleotide sequence.

In the context of the methods and kits according to the invention the nicking endonuclease is preferably a thermostable nicking endonuclease. Nicking endonucleases are commercially available, e.g. from New England Biolabs (NEB). Preferably the nicking endonuclease is selected from the group consisting of Nb.BsmI, Nt.BstNBI, Nt.CviPII, Nb.BbvCI, Nb.BsrDI, Nb.BtsI, Nt.BsmAI, Nt.BbvCI, Nt.BspQI and Nt.AlwI. Nb.BsmI and Nt.BstNBI are particularly preferred nicking endonucleases. Also nicking endonucleases obtained e.g. by genetically engineering standard restriction endonucleases may be used in the context of the present invention. Nb.BsmI is a nicking endonuclease that cleaves only one strand of DNA on a double-stranded DNA substrate; it recognizes the sequence 5'-GAATGC-3' and cuts on the complementary strand as indicated by the slash: 5'-G/CATTC-3'. Nt.BstNBI is a site specific endonuclease that cleaves only one strand of DNA on a double-stranded DNA substrate; it catalyzes a single strand break 4 bases beyond the 3' side of its recognition sequence 5'-GAGTC-3.

Depending on the reaction temperature to be used with the present invention, a suitable nicking endonuclease is selected that is active at this temperature.

In case of a 'primer comprising a tag sequence' ('tagged primer') the 'sequence recognized by a nicking endonuclease' ('nicking endonuclease recognition sequence') may be fully or partially in the tag sequence. The cleavage site may also be in the tag sequence or it may be one or several basepairs (bp) up- or downstream. The cleavage site ('nicking site') may be on the same strand as the indicated recognition sequence or on the other strand.

The method of the invention can in one embodiment be described as comprising the following steps:
  (i) providing a double-stranded template nucleic acid,
  (ii) contacting the template nucleic acid with a helicase for unwinding the double-stranded template nucleic acid to form at least partially single-stranded template nucleic acids,
  (iii) adding oligonucleotide primers for hybridizing to the single-stranded templates of step (ii), wherein at least one oligonucleotide primer comprises a sequence recognized by a nicking endonuclease,
  (iv) synthesising extension products of the oligonucleotide primers which are complementary to the single-stranded template nucleic acids by means of a polymerase to form double-stranded template nucleic acids,
  (v) contacting the double-stranded template nucleic acids synthesized in step (iv) with a nicking endonuclease for introducing a nick in the template nucleic acid,
  (vi) contacting the template nucleic acid of step (v) with a helicase for unwinding the double-stranded template nucleic acid to form at least partially single-stranded template nucleic acids,
  (vii) adding oligonucleotide primers for hybridizing to the single-stranded templates of step (vi),
  (viii) synthesising extension products of the oligonucleotide primers which are complementary to the single-stranded template nucleic acids by means of a polymerase to form double-stranded template nucleic acids,
  (ix) repeating steps (v) to (viii) to amplify the template nucleic acid as required.

In case a single-stranded template nucleic acid is to be amplified, it must be transcribed into a double-stranded nucleic acid, e.g. by reverse transcription or in vitro-transcription.

In a particular embodiment of the method of the invention, the sequence recognized by a nicking endonuclease of the oligonucleotide primer is in a 5' tag sequence that does not hybridize to the template nucleic acid and the method additionally comprises between steps (iv) and (v) the steps of
  (a) contacting the template nucleic acid of step (iv) with a helicase for unwinding the double-stranded template nucleic acid to form at least partially single-stranded template nucleic acids,
  (b) adding oligonucleotide primers for hybridizing to the single-stranded templates of step (a),
  (c) synthesising extension products of the oligonucleotide primers which are complementary to the single-stranded template nucleic acids by means of a polymerase to form double-stranded template nucleic acids.

In FIG. 2 the course of a nicking tHDA reaction on DNA using a tagged primer is schematically illustrated: Step A: dsDNA ('target DNA', 'template DNA') is unwound by a helicase and a primer pair binds to the single stranded DNA. One of the primers has a 5' tag sequence that does not hybridize to the template DNA. A DNA polymerase begins the synthesis of the complementary strands starting from the primers. Step B: Two double-stranded product DNAs are formed: Product 1 based on the untagged primer corresponds to the template DNA and enters the reaction again in step A; product 1' comprises the tag sequence and is unwound by the helicase. Step C: the complementary strands for product 1' are synthesized by the DNA polymerase. Step D: One of the strands results in product 1' and enters the reaction again in step C, the other strand leads to product 2 which comprises the tag sequence with a functional nicking site and nicking enzyme recognition sequence.

Step E: One strand of product 2 is cleaved at the nicking site and unwound by a helicase from the other end. The DNA polymerase elongates the 3' end at the cleavage site and displaces the strand ('strand displacement amplification' (SDA)). A primer binds at the other strand and is elongated by the DNA polymerase. Step F: Primer elongation results in two products, product 3 comprise the tag sequence and product 3' does not comprise the tag sequence. Product 3 is again cleaved at the nicking site, the complementary strand is synthesized. Product 3' is unwound by the helicase. Step G1: The amplification of product 3 leads to product 3 which enters step G1 again and product 3' which enters step G2. Step G2: the complementary strand to both ssDNA strands is synthesized resulting in product 2 and 3' which again enter the reaction at steps E and G2, respectively. The Overall reaction leads to an accumulation of product 3. The products can be detected using hybridization probes e.g. complementary to the reverse strand of the amplicon.

Figure 3:
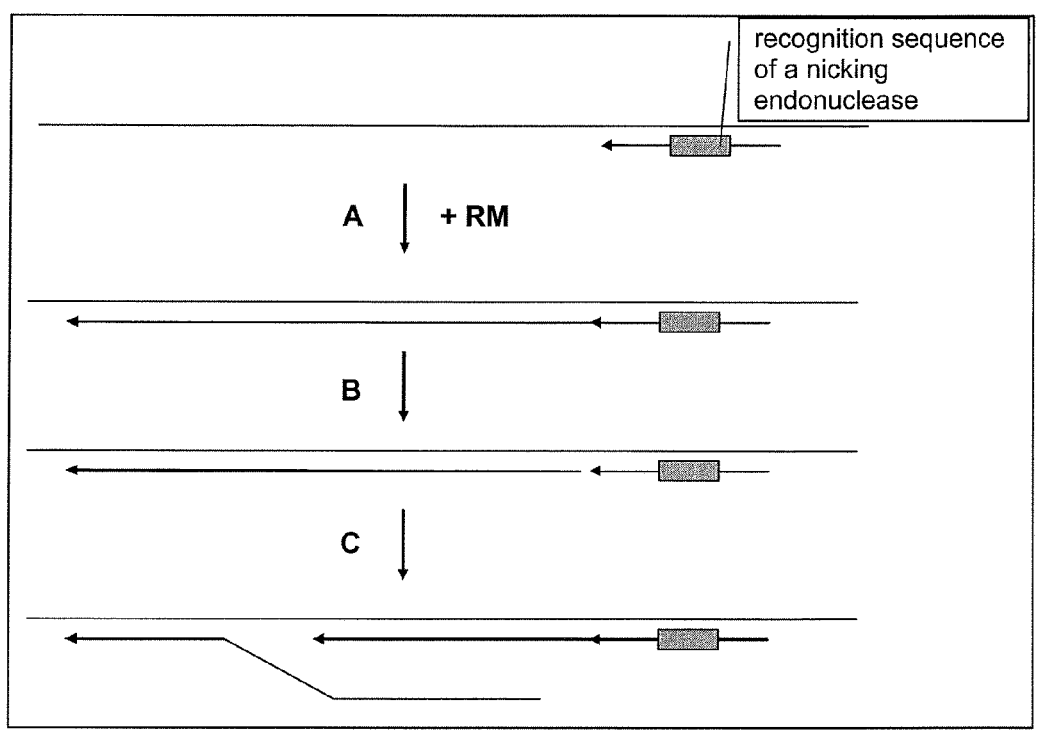
FIG. 3 illustrates the reaction scheme according to a particular embodiment of the nicking tHDA of the present invention using an untagged primer.

In FIG. 3 the course of a nicking tHDA reaction on DNA using an untagged primer is schematically illustrated. Step A: A reaction mix comprising at least one primer, a DNA polymerase, a helicase and a nicking endonuclease is added to dsDNA. The primer comprises a recognition sequence for a nicking endonuclease. The dsDNA is unwound by the helicase, primers hybridize to the single strands and are elongated. A nicking endonuclease recognition site is introduced into one strand. Step B: The resulting dsDNA is cleaved by the nicking endonuclease. Step C: The helicase unwinds the dsDNA and either the old primer or a newly bound primer is elongated at the 3' end by the DNA polymerase.

In the following, typical but only exemplary and non-limiting protocols for one-step and two-step nicking tHDA reactions of DNA are summarized:

Two-Step tHDA Protocol
1. Template DNA and forward and reverse primers are added to a suitable aqueous reaction buffer comprising dNTPs, dATP or ATP, magnesium ions (e.g. as magnesium sulfate, $MgSO_4$), a buffering agent such as Tris HCl, and salts such as NaCl and/or KCl. Micro centrifuge types may for example be used as a reaction container.
2. The reaction mix is heated to a denaturing temperature (e.g. 95° C. for e.g. 2 min), optionally cooled at 4° C. or put on ice, then brought to the actual reaction temperature for a short time (e.g. 64 or 65° C. for e.g. 1 to 3 min). Optionally the reaction mix is then put on ice or 4° C.
3. The enzymes. i.e. the helicase, a DNA polymerase and the nicking enzyme, are added to the reaction mix. The reaction mix can be gently mixed, e.g. by brief vortexing or by pipetting. The enzymes can be premixed in a suitable buffer.
4. The reaction mix is incubated for a suitable time, e.g. 60 to 90 min, preferably 60 to 75 min, at the reaction temperature, e.g. at 64 or 65° C.

One-Step tHDA Protocol
For the one-step protocol step 2 of the two-step protocol is skipped. After step 1 one proceeds directly to step 3.

Typical buffer conditions for the methods of the present invention are as follows:
Tris: 5 to 100 mM, preferably 10 mM
pH 7.5 to 9.5, preferably pH 8.8
KCl: 0 to 50 mM, preferably 5 mM
$MgSO_4$: 1 to 6 mM, preferably 3.5 mM
NaCl: 0 to 100 mM, preferably 40 mM
dNTPs: 0.1 to 1 mM, preferably 0.4 mM
(d)ATP (i.e. dATP and/or ATP): 1 to 7 mM, preferably 3 mM
Primer (forward): 0.02 to 1.5 µM, preferably 0.1 µM
Primer (reverse): 0.02 to 1.5 µM, preferably 0.1 µM
nicking endonuclease: 0.01-10 U/reaction, preferably 0.5 to 3 U/reaction (25 µl reaction)
polymerase: 0.3 to 3 U/µl, preferably 0.6 to 2 U/µl
helicase: 1 to 100 ng/µl, preferably 3 to 20 ng/µl Optionally betaine may be added, preferably in concentrations of from 100 to 2000 mM, preferably 700 to 1200 mM.

However, these are only exemplary conditions that might be adapted depending on other parameters such as the particular enzymes used, the template and/or primer sequences or the temperature.

In a particular embodiment the methods of the invention additionally comprise the step of detecting the amplification product. The amplification product may for example be detected using gel electrophoresis, an intercalating dye, or a specific oligonucleotide probe.

Amplified nucleic acid product may be detected by various methods including ethidium bromide staining and detecting the amplified sequence by means of a label selected from the group consisting of a radiolabel, a fluorescence label, and an enzyme. For example HDA amplified products can be detected in real-time using fluorescence-labelled LUX™ Primers (Invitrogen Corporation, Carlsbad, Calif.) which are oligonucleotides designed with a fluorophore close to the 3' end in a hairpin structure. This configuration intrinsically renders fluorescence quenching capability without separate quenching moiety. When the primer becomes incorporated into double-stranded amplification product, the fluorophore is dequenched, resulting in a significant increase in fluorescent signal.

The oligonucleotide probe preferably comprises a fluorescence label, i.e. a fluorescent dye which typically is covalently attached.

Particularly, the fluorescently labelled probes may be labelled with a dye selected from the group consisting of FAM, VIC, NED, Fluorescein, FITC, IRD-700/800, CY3, CY5, CY3.5, CY5.5, HEX, TET, TAMRA, JOE, ROX, BODIPY TMR, Oregon Green, Rhodamine Green, Rhodamine Red, Texas Red, Yakima Yellow, Alexa Fluor and PET.

Suitable hybridization probes include the LightCycler probe (Roche), the TaqMan probe (Roche), a molecular beacon, a Scorpion primer, a Sunrise primer, a LUX primer and a Amplifluor primer. TaqMn probes are preferred in the context of the present invention.

The present invention also pertains to a kit for amplifying a nucleic acid, comprising
a nicking endonuclease,
a helicase and
a DNA polymerase.

As for the method of the invention, the helicase of the kit is preferably selected from the group consisting of superfamily I helicases such as dda, perA, F-plasmid traI protein helicase and UvrD, superfamily II helicases such as recQ and NS3-helicase, superfamily III helicases such as AAV rep helicase, helicases from dnaB-like superfamily such as T7 phage helicase, and helicases form rho-like superfamily. It is preferred that the helicase is a thermostable helicase. The thermostable Tte-UvrD helicase is particularly preferred.

The polymerase of the kit is preferably selected from the group consisting of Bst DNA polymerase, PyroPhage polymerase, DisplaceAce polymerase and Vent (exo-) Polymerase The nicking endonuclease of the kit is preferably selected from the group consisting of Nb.BsmI, Nt.BstNBI, Nt.CviPII, Nb.BbvCI, Nb.BsrDI, Nb.BtsI, Nt.BsmAI, Nt.BbvCI, Nt.BspQI and Nt.AlwI.

The kit of the invention may further comprise
a buffering agent such as Tris, and/or
dNTPs, and/or
(d)ATP, and/or
a magnesium salt such as magnesium phosphate, and/or
NaCl, and/or
KCl.

The kit of the invention may also comprise a topoisomerase and/or an SSB.

The individual components of the kit may be in one or more containers. Two or more of the components may for example be together in one container, e.g. a reaction tube or vial. The buffering agents, the salts, the dNTPs and—if present—(d)ATP—are preferably in a premixed solution. The kit may also comprise a manual.

The invention further relates to the use of the methods and the kits according to the invention for the amplification and/or detection of nucleic acids. The methods and kits may for example be used for the detection of microorganism, viruses, pathogens, human genomic DNA, cDNA and the like. The samples from which the nucleic acids are detected may for example be clinical samples e.g. a bodily fluid such as blood, plasma, serum and urine, or may be samples from the environment, plants, animals, from livestock, foodstuff or from a crime scene. The methods and kits may for instance be used in a dedicated laboratory, at the point of care or in the field. Nucleic acids may be purified and/or isolated from the samples prior to amplification or they may be amplified and/or detected directly in the sample.

The following examples illustrate particular embodiments of the present invention, however without being limiting.

EXAMPLES

Example 1

Nicking tHDA Using a Tagged Primer

In this example, a sequence (SEQ ID NO:1) from the porin gene of the *Neisseria gonorrhoeae* genome has been amplified and detected using standard tHDA and the nicking tHDA method according to the invention, respectively:

(SEQ ID NO: 1)
5'-ATTTGTTCCGAGTCAAAACAGCAAGTCCGCCTATACGCCTGCTACTT
TCACGCTGGAAAGTAATCAGATGAAACCAGTTCCG-3' a) Materials:

TABLE 1

Primers and probes for amplification and detection of SEQ ID NO: 1

| Oligo ID | Sequence (5'→3') | Tm (NN) |
|---|---|---|
| PorA F5 | ATTTGTTCCGAGTCAAAACAGCAAGTC (SEQ ID NO: 2) | 63° C. |
| PorA R5 | CGGAACTGGTTTCATCTGATTACTTTC (SEQ ID NO: 3) | 62° C. |
| PorA5_VD5 FAM | 6-FAM // CGCCTATACGCCTGCTACTTTCACG // BHQ1 (SEQ ID NO: 4) | 68° C. |
| porA_NS | CGGGGCGTCTGGAAGGCGCATTCCGGAACTGGTTTCATCTGATTACTTTC (SEQ ID NO: 5) | |

Tm: melting temperature; standard tHDA: primers PorA F5 and PorA R5, probe PorA5_VD5 FAM (labeled with 6-FAM and BHQ1); nicking tHDA: primers PorA F5 and porA_NS, probe PorA5_VD5 FAM (labeled with 6-FAM and BHQ1)

TABLE 2

Premix 1 for standard tHDA and nicking tHDA of *N. gonorrhoeae* genomic DNA using the primers of table 1

| Component | Stock | Final Conc. | standard tHDA | | Nicking tHDA, w/o Nb · BsmI | | Nicking tHDA, w/Nb · BsmI | |
|---|---|---|---|---|---|---|---|---|
| | | | 1 | 2 | 3 | 4 | 5 | 6 |
| *N. gonorrhoeae* gDNA (1 ng/μl) | | | 1 | — | 1 | — | 1 | — |
| PorA F5 | 2.5 μM | 75 nM | 0.75 | 0.75 | 0.75 | 0.75 | 0.75 | 0.75 |
| PorA R5 | 2.5 μM | 150 nM | 1.5 | 1.5 | — | — | — | — |
| porA_NS | 2.5 μM | 150 nM | — | — | 1.5 | 1.5 | 1.5 | 1.5 |
| PorA Pro | 2.5 μM | 60 nM | 0.6 | 0.6 | 0.6 | 0.6 | 0.6 | 0.6 |
| reaction mix (see | | 1x | 4.85 | 4.85 | 4.85 | 4.85 | 4.85 | 4.85 |

TABLE 2-continued

Premix 1 for standard tHDA and nicking tHDA of N. gonorrhoeae genomic DNA using the primers of table 1

| Component | Stock | Final Conc. | standard tHDA | | Nicking tHDA, w/o Nb · BsmI | | Nicking tHDA, w/Nb · BsmI | |
|---|---|---|---|---|---|---|---|---|
| | | | 1 | 2 | 3 | 4 | 5 | 6 |
| below) RNAse-free H₂O | | | 13.3 | 14.3 | 13.3 | 14.3 | 13.3 | 14.3 |

Reaction Mix:
2.5 µl 10× annealing Buffer
0.2 µl 5M NaCl
0.4 µl 25 mM dNTP mix
0.75 µl 100 mM dATP
1 µl 100 mM MgSO₄
10× Annealing Buffer:
100 mM KCl
200 mM Tris/HCl pH 8.8

TABLE 3

Premix 2 for standard tHDA and nicking tHDA of N. gonorrhoeae genomic DNA using the primers and reagents of tables 1 and 2

| | Stock | Final conc. | standard tHDA | | Nicking tHDA, w/o Nb · BsmI | | Nicking tHDA, w/Nb · BsmI | |
|---|---|---|---|---|---|---|---|---|
| | | | 1 | 2 | 3 | 4 | 5 | 6 |
| HDA Enzyme Mix (IsoAmp Kit, NEB) | | | 1.75 | 1.75 | 1.75 | 1.75 | 1.75 | 1.75 |
| Nb · BsmI | 10 U/µl | 0.4 U/µl | — | — | — | — | 1 | 1 |
| RNAse-free H₂O | | | 1.25 | 1.25 | 1.25 | 1.25 | 0.25 | 0.25 |

Figure 4:
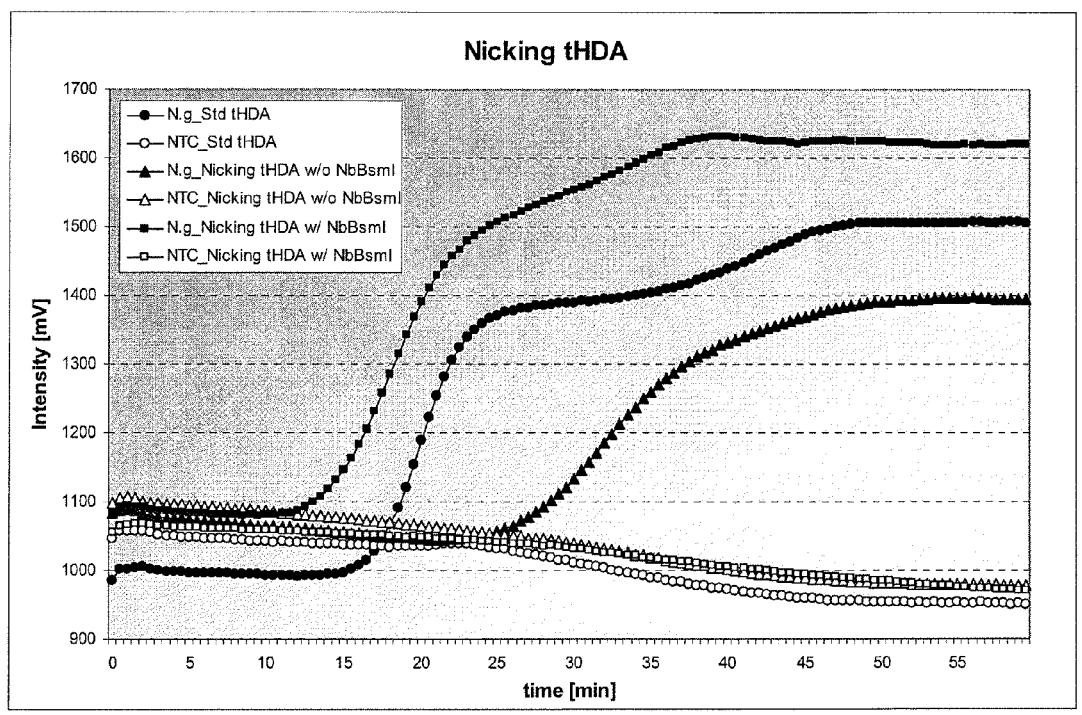
FIG. 4 shows the results (amplification plots) of the different Real Time (nicking) tHDA reactions from Example 1 at the Tube Scanner. Shown are the raw fluorescence intensities over time.
Figure 5A:
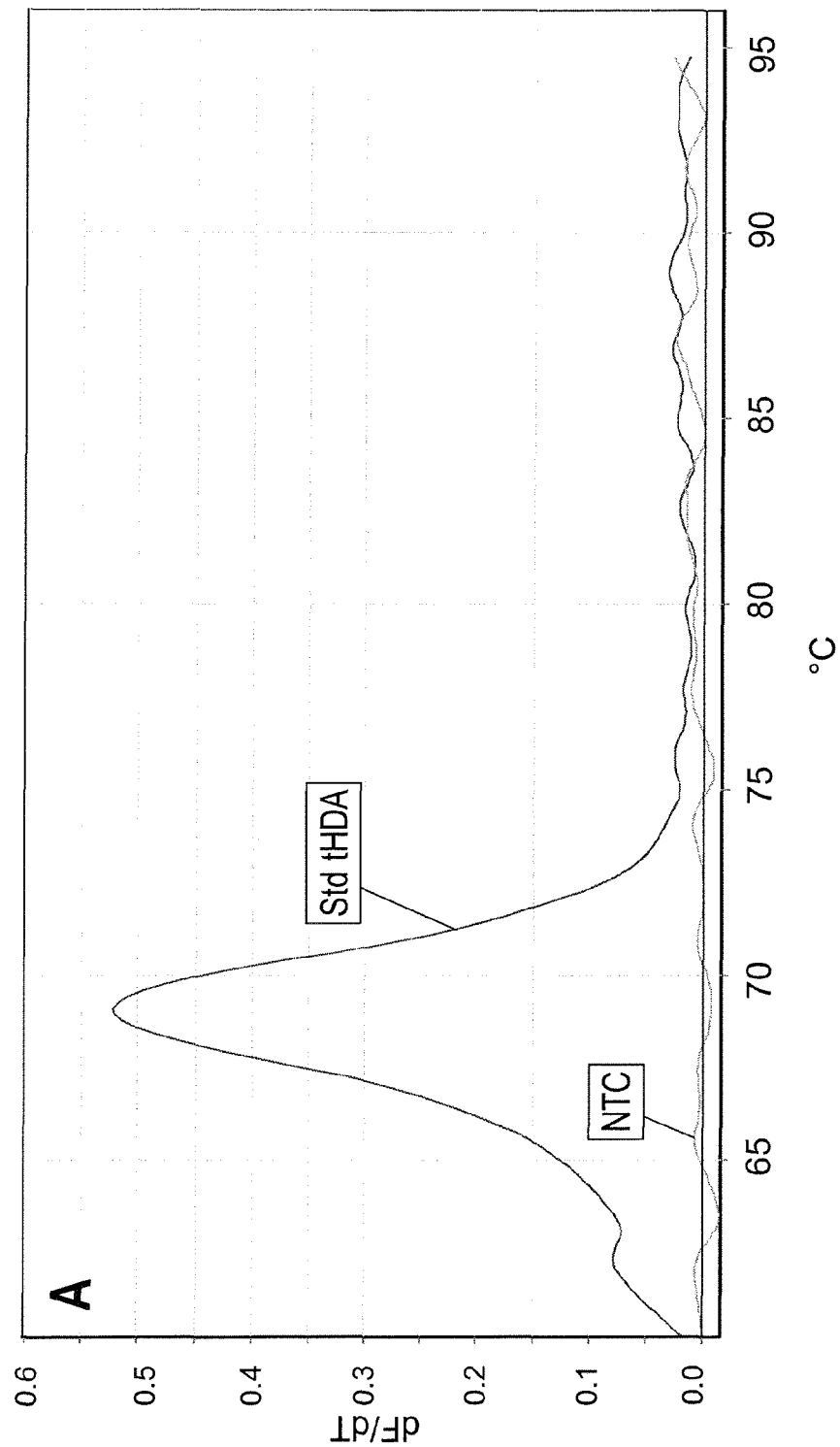
FIG. 5 shows the melting curves of the amplification products of Example 1. A) standard tHDA, B) nicking tHDA without Nb.BsmI, C) nicking tHDA with Nb.BsmI.
Figure 5B:
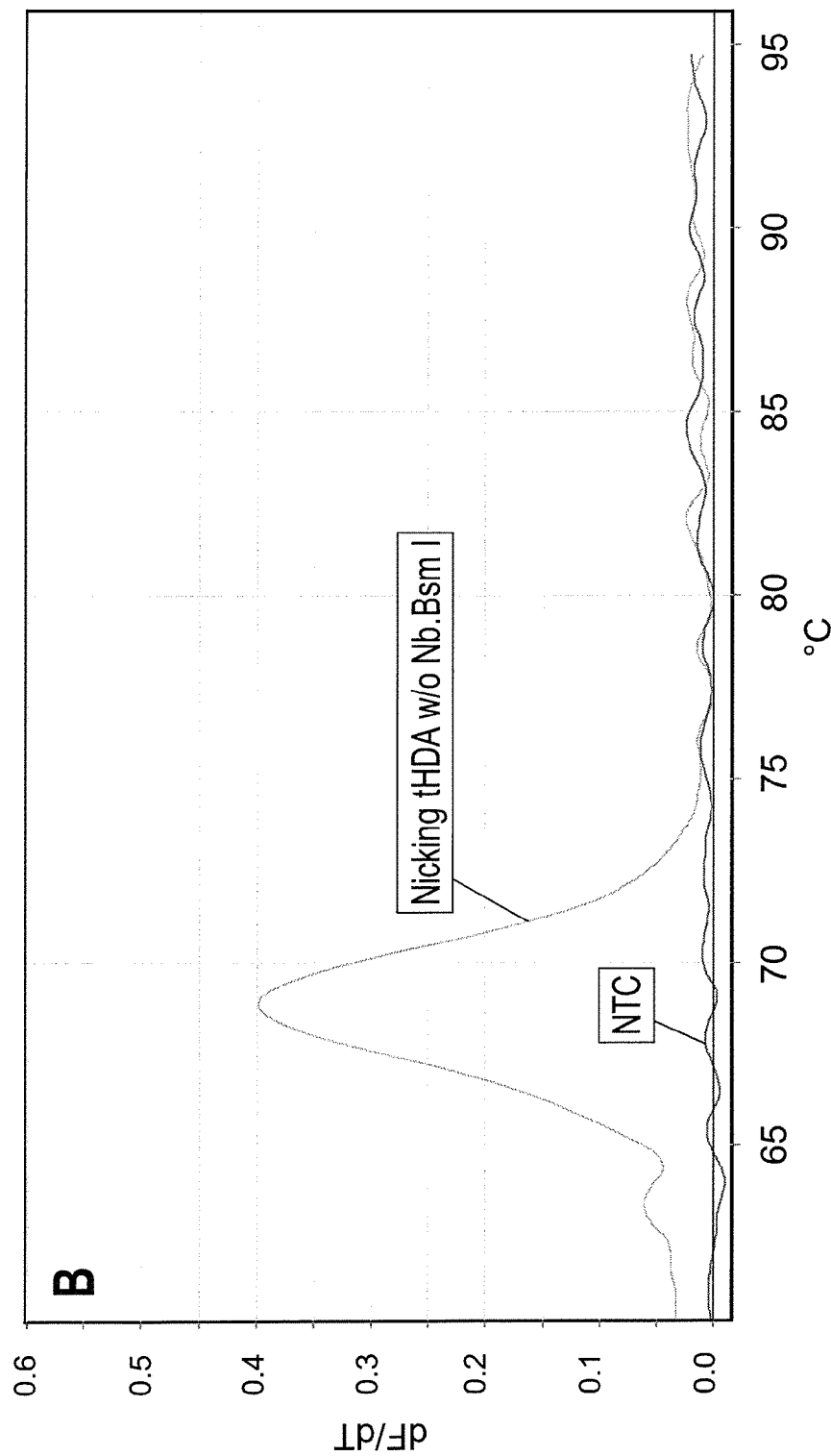
Figure 5C:
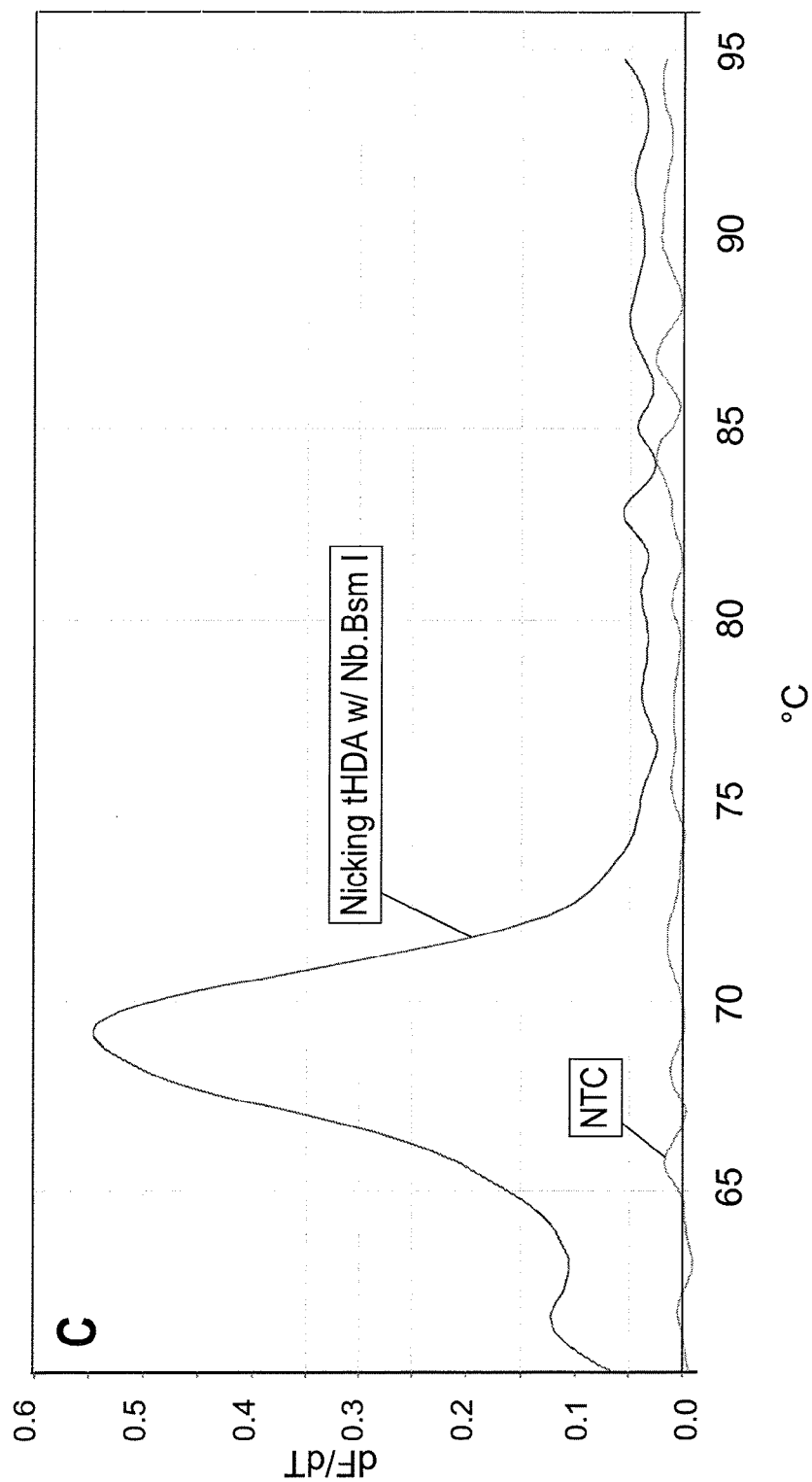

12% Polyacrylamide Gel for Electrophoresis:
12 ml 30% Acrylamide/Bis-acrylamide 29:1
3 ml TBE
13 ml H2O
150 µl 10% APS
40 µl TEMED a) Methods:
  22 µl of Premix 1 were pipetted into 8×PCR strips
  2 min denaturation step at 95° C. in PCR-Cycler, followed by immediate cooling at 4° C.
  the strip was then incubated for 1 min in a Tube Scanner (ESE GmbH) at 65° C.
  3 µl of each Premix 2 was pipetted into the lid of the strip centrifuged after closing
  the reaction mixtures were mixed by shaking, again centrifuged and placed in the Tube Scanner
  the tubes were then incubated for 60 min at 65° C., fluorescence was read out every 30 sec
  subsequently 10 µl of each reaction was transferred into a RotorGene Tube and melting curves were measured using a RotorGene Q (QIAGEN GmbH) (55-95° C., increment 0.5° C., hold 5")
  4 µl of each reaction was loaded onto a 12% polyacrylamide gel (70 min, 140 V)

c) Results:
I) Real Time (Nicking) tHDA:
  FIG. 4 shows the results (amplification plots) of the different Real Time (nicking) tHDA reactions at the Tube Scanner. Shown are the raw fluorescence intensities over time.
  all non-template control reactions (NTCs) showed no unspecific amplification
  the amplification curve for the standard tHDA had a take-off point at around 15 min
  the amplification curve for the nicking tHDA without (w/o) Nb.BsmI had a take-off point at 24 min and a considerably smaller slope as compared to the other two curves
  the amplification curve for the nicking tHDA with (w/) Nb.BsmI had a take-off point at around 11 min II) Melting Curves:
  FIG. 5 shows the melting curves of the amplification products. A) standard tHDA, B) nicking tHDA without Nb.BsmI, C) nicking tHDA with Nb.BsmI.
  For all reactions comprising a target (template) DNA a specific amplification product could be identified by the melting temperature (Tm). In all NTC reactions no detectable amplicon was observed.

Figure 6:
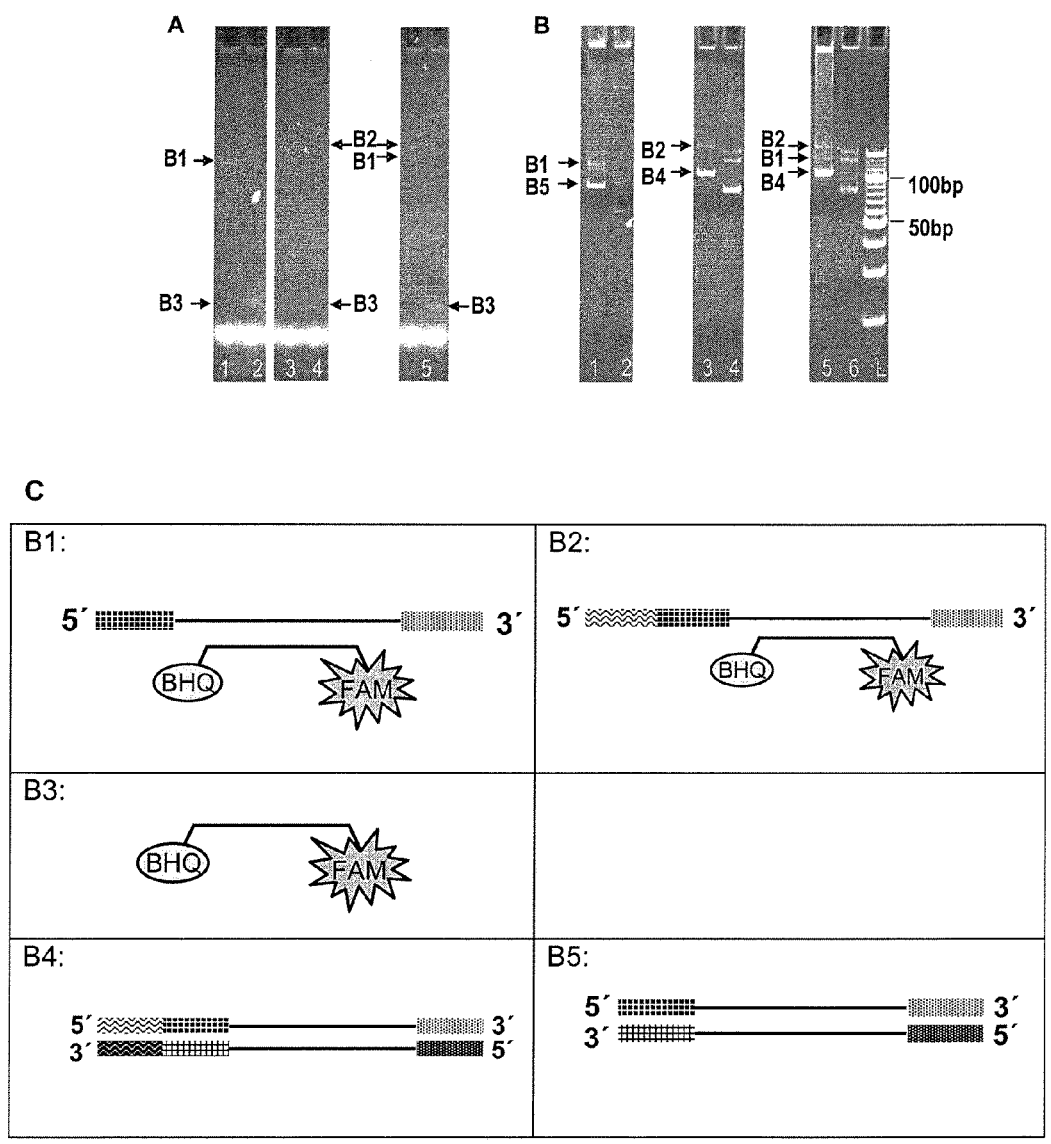
FIG. 6 shows the polyacrylamide gel with the individual reaction mixtures of Example 1 after amplification and electrophoresis. A) Gel before staining, B) after staining with EtBr. C) The contents of the individual bands B1 to B5 on the gel have also been graphically illustrated in FIGS. 6B1 to 6B5.

III) Polyacrylamide Gels:
  FIG. 6 shows the polyacrylamide gel with the individual reaction mixtures after amplification and electrophoresis. A) Gel before staining, B) after staining with EtBr. The contents of the individual bands B1 to B5 on the gel have also been graphically illustrated in FIGS. 6B1 to 6B5.
  lane 1: N. gonorrhoeae gDNA standard tHDA
  lane 2: NTC standard tHDA
  lane 3: N. gonorrhoeae gDNA nicking tHDA w/o Nb.BsmI
  lane 4: NTC nicking tHDA w/o Nb.BsmI
  lane 5: N. gonorrhoeae gDNA nicking tHDA w/ Nb. BsmI
  lane 6: NTC nicking tHDA w/ Nb. BsmI
  L: 10 bp ladder (size marker)
  Bands on the unstained gel (FIG. 6A) are due to fluorescently labelled probes. These bands demonstrate the expected dependency of the products on the initial amount of primer and nicking endonuclease (B1-B3).
  On the stained gel significant bands are visible for the dsDNA amplification products (B4, B5), as well as the hybridisation products with the probes that are also visible on the unstained gel (B1-B3). All NTC reactions also showed bands which, however, did not result in a false positive signal in the Tube Scanner or Tm analysis because of their unspecific sequence in this mode of detection (specific hybridisation of the ssDNA reverse strand with the probe). All NTC reactions also showed no band in the unstained gel, which would be indicative for a hybridisation with the probe.

Example 2

Nicking tHDA Using an Untagged Primer a) Target Sequence

The target sequence (SEQ ID NO:6) is derived from the mRNA of the human p53 gene and comprises nucleotide residues 322 to 395 of sequence NM001126114.

For the design of a primer comprising a sequence recognized by a nicking endonuclease, the original sequence of the reverse primer HDA-TP53rev has been modified, so that the primer sequence HDA-TP53rev7 was created. This introduced a recognition sequence for the enzyme Nt.BstNBI (see FIG. 7).

TABLE 4

Primer sequences for the amplification of

| Primer ID | Seq ID | Sequence 5'→3' |
|---|---|---|
| HDA-TP53for | SEQ ID NO: 7 | ATTTGATGCTGTCCCCGGACGATATT |
| HDA-TP53rev | SEQ ID NO: 8 | CATTCTGGGAGCTTCATCTGGACCGT |
| HDA-TP53rev7 | SEQ ID NO: 9 | CATTCTGGGAGTCTCATCTGGACCTG | b) Amplification of p53 from Human cDNA
Materials:

For this reaction, human RNA has been transcribed into cDNA. For the tHDA reaction cDNA from 10 ng RNA has been used. The reaction has been performed in the buffer (reaction mix) outlined in table 5.

TABLE 5

Reaction mix for tHDA amplification of p53 cDNA

| Tris, pH 8.8 | 10 mM |
|---|---|
| KCl | 5 mM |
| MgSO$_4$ | 3.5 mM |
| NaCl | 40 mM |
| dNTPs | 0.4 mM |
| dATP | 3 mM |
| Betaine | 975 mM |
| Primer HDA-TP53 | 0.1 µM |
| Primer HDA-TP53rev7 | 0.1 µM |
| Nt.BstNBI nicking endonuclease | 0-10 U/reaction |
| Bst polymerase | 1 U/µl |
| helicase | 10 ng/µl |

Figures 7, 8:
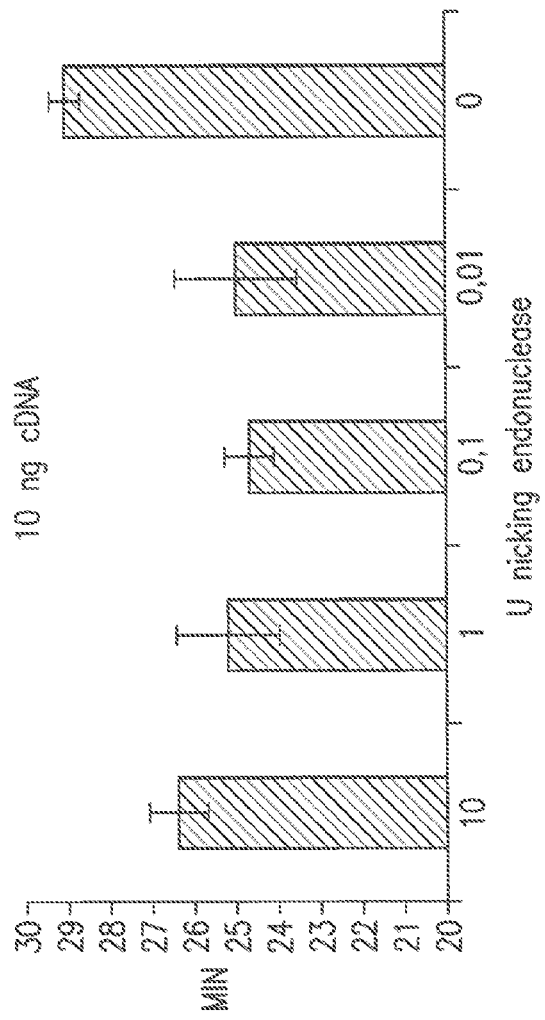
FIG. 7 shows the sequences of the target DNA of Example 2 together with the primers used.
FIG. 8 illustrates the dependency of the reaction rate on the concentration of nicking endonuclease. Shown is the time in minutes (min) until a signal of the amplicon could be detected that is significantly above the background signal. In the presence of lower concentrations of nicking endonuclease the signal has been detected about 5 min earlier than for the reaction without a nicking endonuclease, indicating a faster reaction.

The reaction mix has been set-up on ice and subsequently performed in a real-time PCR cycler for 60 min at 65° C.
Results:

FIG. 8 illustrates the dependency of the reaction rate on the concentration of nicking endonuclease. Shown is the time in minutes (min) until a signal of the amplicon could be detected that is significantly above the background signal. In the presence of lower concentrations of nicking endonuclease the signal has been detected about 5 min earlier than for the reaction without a nicking endonuclease, indicating a faster reaction.

Figure 9:
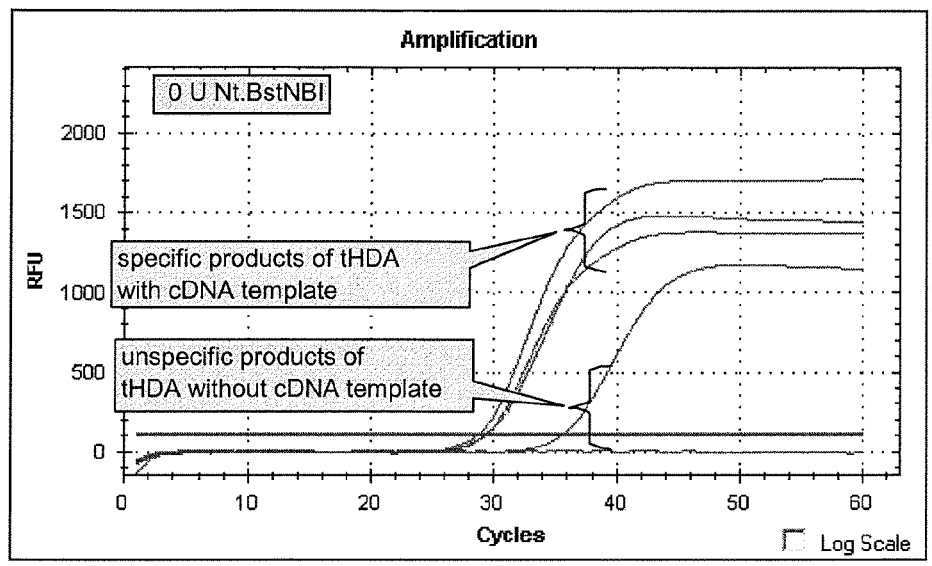
FIG. 9 shows the amplification curves (fluorescence over time) for a standard tHDA, i.e. without any nicking endonuclease. Three curves were measured in the presence of the cDNA template, two curves have been measured without the presence of a cDNA template.

FIG. 9 shows the amplification curves (fluorescence over time) for a standard tHDA, i.e. without any nicking endonuclease. Three curves were measured in the presence of the cDNA template, two curves have been measured without the presence of a cDNA template.

Figure 10:
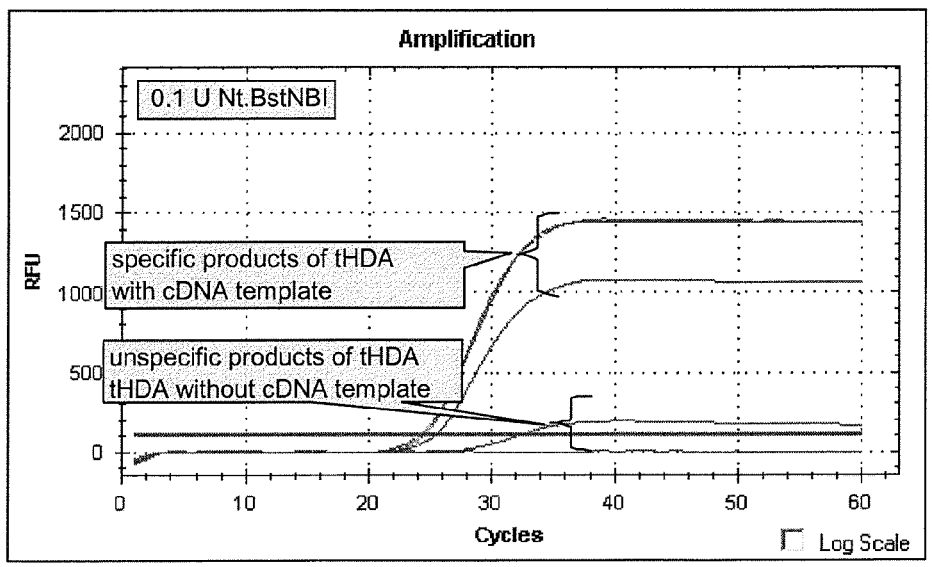
FIG. 10 shows the amplification curves of a tHDA in the presence of 0.1 U nicking endonuclease Nt.BstNBI. Three curves have been measured in the presence of a cDNA template, two curves have been measured in the absence of a cDNA template.

FIG. 10 shows the amplification curves of a tHDA in the presence of 0.1 U nicking endonuclease Nt.BstNBI. Three curves have been measured in the presence of a cDNA template, two curves have been measured in the absence of a cDNA template.

Figure 11:
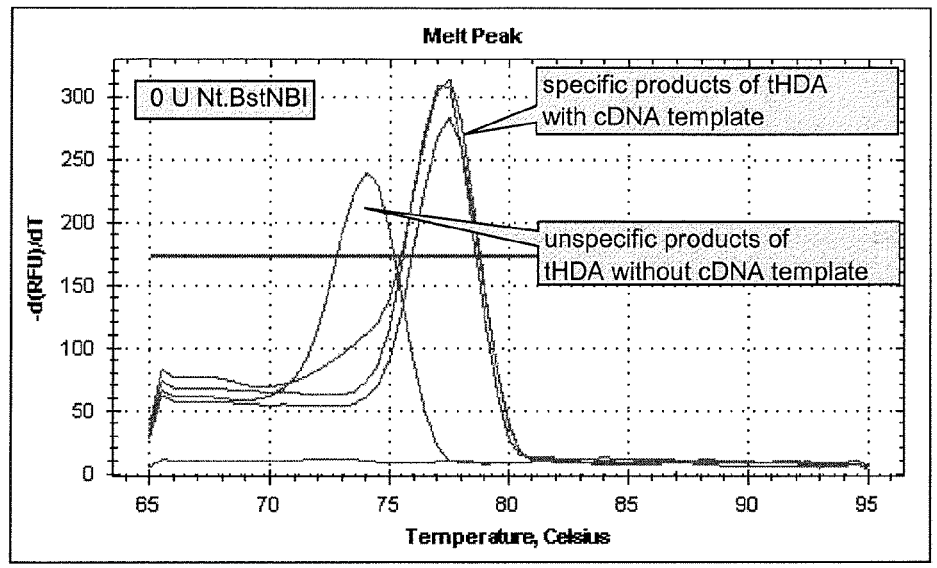
FIG. 11 shows a melting curve analysis after a standard tHDA without nicking endonuclease Nt.BstNBI. The melting curve analysis has been performed with the reactions that are shown in FIG. 9. Three curves have been measured in the presence of the cDNA template, two curves have been measured in the absence of a cDNA template.

FIG. 11 shows a melting curve analysis after a standard tHDA without nicking endonuclease Nt.BstNBI. The melting curve analysis has been performed with the reactions that are shown in FIG. 9. Three curves have been measured in the presence of a cDNA template, two curves have been measured in the absence of a cDNA template.

Figure 12:
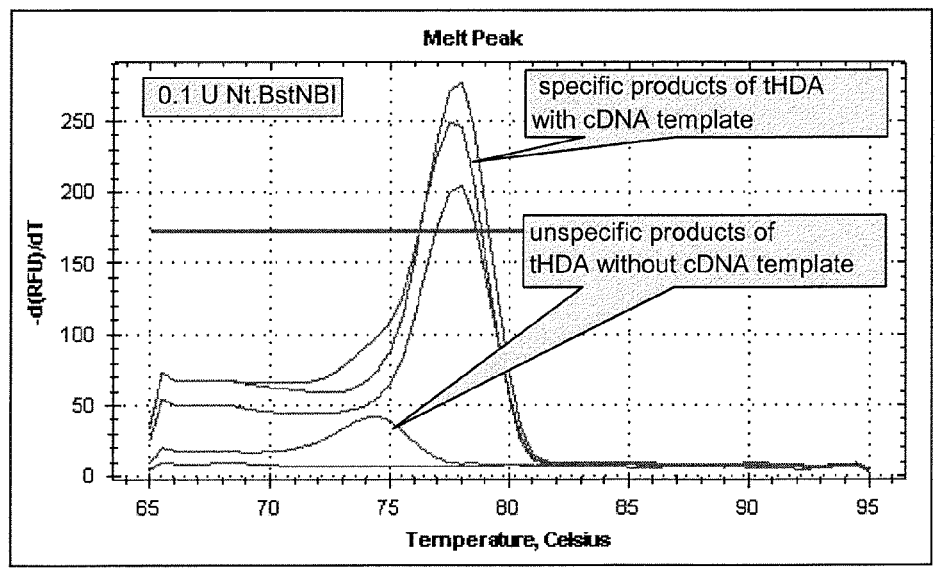
FIG. 12 shows a melting curve analysis after a standard tHDA in the presence of 0.1 U nicking endonuclease Nt.BstNBI. The melting curve analysis has been performed with the reactions that are shown in FIG. 10. Three curves have been measured in the presence of a cDNA template, two curves have been measured in the absence of a cDNA template.

FIG. 12 shows a melting curve analysis after a standard tHDA in the presence of 0.1 U nicking endonuclease Nt.BstNBI. The melting curve analysis has been performed with the reactions that are shown in FIG. 10. Three curves have been measured in the presence of a cDNA template, two curves have been measured in the absence of a cDNA template.

c) Amplification of p53 from Human Genomic DNA (gDNA)

100 ng human genomic DNA have been used for this reaction and have been denatured in a 95° C. heating step. The reaction has been performed in the reaction buffer as outlined in Table 6.

TABLE 6

Reaction mix for tHDA amplification of p53 gDNA

| Tris, pH 8.8 | 10 mM |
|---|---|
| KCl | 5 mM |
| MgSO$_4$ | 3.5 mM |
| NaCl | 40 mM |
| dNTPs | 0.4 mM |
| dATP | 3 mM |
| Betaine | 975 mM |
| Primer HDA-TP53 | 0.1 µM |
| Primer HDA-TP53rev7 | 0.1 µM |
| Nt.BstNBI Nicking Endonuklease | 0-0.4 U/µl |
| Bst polymerase | 1 U/µl |
| Helicase | 10 ng/µl |

Figure 13:
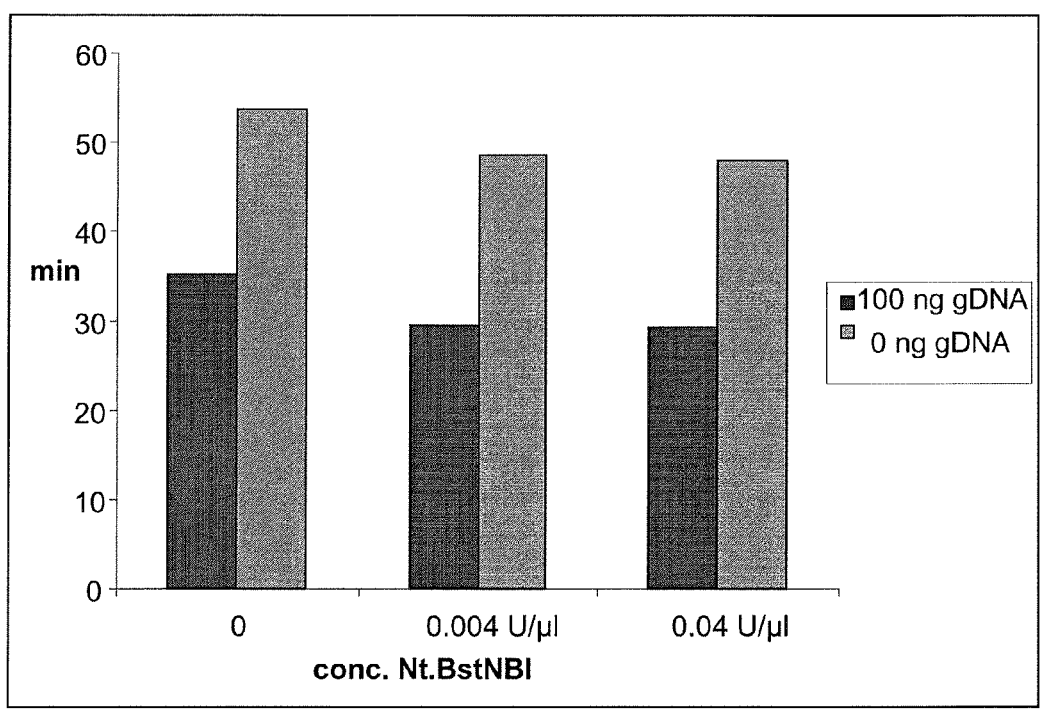
FIG. 13 illustrates the dependency of the reaction rate on the presence of nicking endonuclease. Shown is the time in minutes (min) until a signal of the amplicon could be detected that is significantly above the background signal. In the presence of nicking endonuclease the signal has been detected about 6 min earlier than for the reaction without a nicking endonuclease, indicating a faster reaction.
Figure 14A:
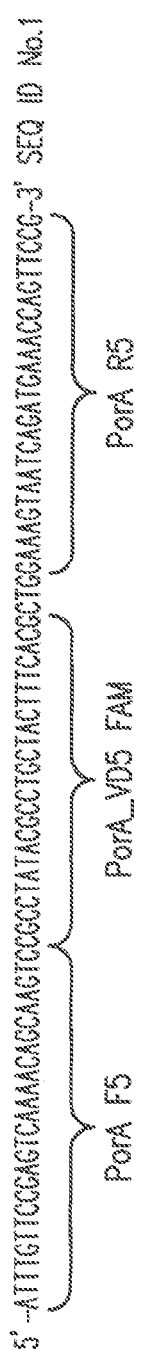
FIG. 14 illustrates the sequences of one strand of the amplicons of Example 1 which relate to a portion of the porin gene of the *Neisseria gonorrhoeae* genome. The hybridization regions of the primers and probes are indicated. (A): standard tHDA; (B): nicking tHDA according to the method of the present invention using a tagged primer, underlined is the recognition sequence of Nb.BsmI, the sequence introduced by the tagged primer is in italics.
Figure 14B:
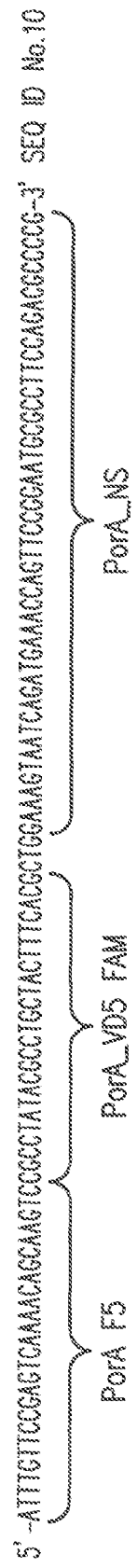

The reaction mix has been set-up on ice and subsequently performed in a real-time PCR cycler for 60 min at 65° C.
Results:

FIG. 13 illustrates the dependency of the reaction rate on the presence of nicking endonuclease. Shown is the time in minutes (min) until a signal of the amplicon could be detected that is significantly above the background signal. In the presence of nicking endonuclease the signal has been detected about 6 min earlier than for the reaction without a nicking endonuclease, indicating a faster reaction.

The invention claimed is:

1. A method for amplifying a template nucleic acid, comprising:
   (a) providing a template nucleic acid,
   (b) contacting the template nucleic acid with a helicase,
   (c) hybridizing an oligonucleotide primer to the template nucleic acid, and
   (d) amplifying said template nucleic acid using the helicase dependent amplification (HDA) reaction, said HDA reaction introducing a recognition sequence into the template nucleic acid,
   said HDA reaction occurring in the presence of a nicking endonuclease that recognizes a nucleotide sequence of a completely or partially double-stranded nucleic acid molecule and cleaves only one strand of the template nucleic acid at a specific location relative to the recognition sequence,
   wherein the HDA reaction is a thermophilic HDA (tHDA), and wherein the template nucleic acid is shorter than 400 bp.

2. The method according to claim 1, wherein said oligonucleotide primer comprises a 5' tag sequence that does not hybridize to the template nucleic acid and the recognition sequence is in said tag sequence.

3. The method according to claim 1, wherein the template nucleic acid is a double-stranded template nucleic acid.

4. The method according to claim 1, wherein the helicase is selected from the group consisting of dda, pcrA, F-plasmid traI protein helicase, UvrD, recQ, NS3-helicase, AAV rep helicase, T7 phage helicase, and rho-like superfamily helicase.

5. The method according to claim 1, wherein a polymerase in the HDA is selected from the group consisting of Bst DNA polymerase, PyroPhage polymerase, DisplaceAce polymerase and Vent (exo-) Polymerase.

6. The method according to claim 1, wherein the nicking endonuclease is selected from the group consisting of Nb.BsmI, Nt.BstNBI, Nt.CviPII, Nb.BbvCI, Nb.BsrDI, Nb.BtsI, Nt.BsmAI, Nt.BbvCI, Nt.BspQI and Nt.AlwI.

7. The method according claim 1, wherein the HDA amplification reaction is performed at a temperature above 50° C.

8. The method according to claim 1, additionally comprising heating the template nucleic acid prior to the amplifying in (d).

9. The method according to claim 1, additionally comprising detecting a product of the amplifying.

10. The method according to claim 9, wherein the product is detected using gel electrophoresis, an intercalating dye, or a specific oligonucleotide probe.

11. A method for amplifying a template nucleic acid, comprising:
- (a) providing a template nucleic acid,
- (b) contacting the template nucleic acid with a helicase, and
- (c) amplifying said template nucleic acid using the helicase dependent amplification (HDA) reaction, the template nucleic acid comprising a recognition sequence, said HDA reaction occurring in the presence of a nicking endonuclease that recognizes a nucleotide sequence of a completely or partially double-stranded nucleic acid molecule and cleaves only one strand of the template nucleic acid at a specific location relative to the recognition sequence, wherein the HDA reaction is a thermophilic HDA (tHDA), and wherein the template nucleic acid is shorter than 400 bp.

12. The method according to claim 11, wherein the template nucleic acid is a double-stranded template nucleic acid.

13. The method according to claim 11, wherein the helicase is selected from the group consisting of dda, pcrA, F-plasmid traI protein helicase, UvrD, recQ, NS3-helicase, AAV rep helicase, T7 phage helicase, and rho-like superfamily helicase.

14. The method according to claim 11, wherein a polymerase in the HDA is selected from the group consisting of Bst DNA polymerase, PyroPhage polymerase, DisplaceAce polymerase and Vent (exo-) Polymerase.

15. The method according to claim 11, wherein the nicking endonuclease is selected from the group consisting of Nb.BsmI, Nt.BstNBI, Nt.CviPII, Nb.BbvCI, Nb.BsrDI, Nb.BtsI, Nt.BsmAI, Nt.BbvCI, Nt.BspQI and Nt.AlwI.

16. The method according claim 11, wherein the HDA amplification reaction is performed at a temperature above 50° C.

17. The method according to claim 11, additionally comprising heating the template nucleic acid prior to the amplifying in (c).

18. The method according to claim 11, additionally comprising detecting a product of the amplifying.

19. The method according to claim 18, wherein the product is detected using gel electrophoresis, an intercalating dye, or a specific oligonucleotide probe.

* * * * *